United States Patent
Jung et al.

(10) Patent No.: US 9,656,100 B2
(45) Date of Patent: May 23, 2017

(54) ION GENERATING APPARATUS, AND TREATING APPARATUS AND TREATING METHOD USING THE SAME

(71) Applicant: ELECTRONICS AND TELECOMMUNICATIONS RESEARCH INSTITUTE, Daejeon (KR)

(72) Inventors: Moon Youn Jung, Daejeon (KR); Won Bae Cho, Daejeon (KR)

(73) Assignee: ELECTRONICS & TELECOMMUNICATIONS RESEARCH INSTITUTE, Daejeon (KR)

( * ) Notice: Subject to any disclaimer, the term of this patent is extended or adjusted under 35 U.S.C. 154(b) by 0 days.

(21) Appl. No.: 15/044,986

(22) Filed: Feb. 16, 2016

(65) Prior Publication Data

US 2016/0236011 A1   Aug. 18, 2016

(30) Foreign Application Priority Data

Feb. 16, 2015 (KR) .................. 10-2015-0023317
Jan. 5, 2016 (KR) .................. 10-2016-0001021

(51) Int. Cl.
H01J 27/24 (2006.01)
H01J 27/02 (2006.01)
A61N 5/10 (2006.01)

(52) U.S. Cl.
CPC ......... *A61N 5/1077* (2013.01); *A61N 5/1075* (2013.01); *A61N 2005/1052* (2013.01); *A61N 2005/1088* (2013.01)

(58) Field of Classification Search
USPC .............. 250/396 R, 423 P, 423 R, 424
See application file for complete search history.

(56) References Cited

U.S. PATENT DOCUMENTS

| | | | | |
|---|---|---|---|---|
| 7,781,744 B2* | 8/2010 | Bedeschi | ............... | G21G 1/001 250/423 R |
| 8,624,502 B2* | 1/2014 | Rosenthal | ............... | H01J 27/18 250/423 R |
| 2010/0289409 A1* | 11/2010 | Rosenthal | ............... | H01J 27/18 315/111.81 |
| 2012/0211668 A1* | 8/2012 | Okamura | ................ | A61N 5/10 250/396 R |
| 2013/0138184 A1* | 5/2013 | Jung | .................... | A61N 5/1077 607/100 |

FOREIGN PATENT DOCUMENTS

KR  10-2013-0060614 A  6/2013
KR  10-2013-0103284 A  9/2013

* cited by examiner

*Primary Examiner* — Bernard Souw

(57) ABSTRACT

Provided is a treating apparatus including an ion generating apparatus configured to inject ionized elements into a diagnosis subject to remove a tumor in the diagnosis subject, and an image photographing apparatus configured to measure positions of the ionized elements in the diagnosis subject. The ion generating apparatus includes a target including a first element and a first isotope that is a radioactive isotope of the first element, and a laser configured to allow a laser beam to be incident on the target and thus ionize the first element and the first isotope.

23 Claims, 6 Drawing Sheets

ION GENERATING APPARATUS, AND TREATING APPARATUS AND TREATING METHOD USING THE SAME

CROSS-REFERENCE TO RELATED APPLICATIONS

This U.S. non-provisional patent application claims priority under 35 U.S.C. §119 of Korean Patent Application No. 10-2015-0023317, filed on Feb. 16, 2015 and Korean Patent Application No. 10-2016-0001021, filed on Jan. 5, 2016, the entire contents of which are hereby incorporated by reference.

BACKGROUND

The present disclosure herein relates to an ion generating apparatus, and a treating apparatus and a treating method using the same to remove a tumor.

As radiation treating methods, there are X-ray, electron beam, and ion beam treating methods, and the like. Since the X-ray treating method is an inexpensive method which may be embodied by using a simple apparatus, the X-ray treating method is universally used among the radiation treating methods. Treating of a tumor in the case where electrons are accelerated by an accelerator to be injected into the tumor was proved in 1950s. However, the electron beam treatment settled as a method of radiation treatment in earnest by realizing a size reduction of an electron accelerator in 1980s. Meanwhile, the X-ray treatment or electron beam treatment breaks a hydrogen bond in a cancer cell to destroy DNA of a cancer, which entails a side effect of seriously damaging healthy cells existing on a progress path. As a method for reducing a limitation of exposure to normal cells, a technology such as intensity-modulated radiation therapy (IMRT), tomo-therapy, and cyber knife has been developed, but these did not completely solve the aforementioned side effect.

The ion beam treating method receives attention as treating means for reducing the side effect of the X-ray treatment or the electron beam treatment. An ion beam should be accelerated to have a high speed like the electrons in order to permeate a material. Even though the speed of the ion beam is gradually reduced in the case where the ion beam permeates a predetermined material, immediately before the ion beam is stopped, the largest energy loss of ionizing radiation occurs. This phenomenon is called a Bragg peak named for William Henry Bragg finding this in 1903. Therefore, in the case of the ion beam treating method, when the speed of the ions is precisely controlled, selective and local treatment to malignant tumors is feasible. In the case where the tumor is positioned deeply in the body, protons or ions having very high energy should be accelerated from the outside of the body. Among methods for accelerating the protons or ions, there is a laser driven ion acceleration method. If high power laser beam is irradiated on a thin film, ions or protons of the thin film escape with acceleration energy to the outside of the thin film by a target normal sheath acceleration model (TNSA model) or a radiation pressure acceleration model (RPA model). The escaping ions permeate a patient's body by energy of the ions, and are stopped at a predetermined depth at which the tumor is positioned, and active oxygen (free oxygen radical) is generated in a large amount in a stop area to necrotize the tumor cells. This is a typical ion beam treating principle.

In the ion beam treating method using the laser driven ion acceleration method, two properties are required in the ions. In order to inject the ions deeply into the body, it is required that the ions are charged particles in a high energy state and the most charged particles have the same energy. As an example, protons having energy of about 250 MeV may permeate a human body by about 20 cm. In the case of ocular cancer treatment, charged particles having high energy of about 70 MeV are required, and in order to treat a cancer positioned deeply in the body, charged particles having high energy of about 200 MeV or more are required. In this case, the protons and the ions driven by the laser should have uniform energy.

SUMMARY

The present disclosure provides an ion generating apparatus, and a treating apparatus and a treating method including the same, in which a tumor in a diagnosis subject is removed and simultaneously a forming position of a Bragg peak in the diagnosis subject is diagnosed.

The tasks to be solved by an embodiment of the inventive concept are not limited to the aforementioned tasks, and other unmentioned tasks may be clearly understood by a person with skill in the art from the following description.

An embodiment of the inventive concept provides a treating apparatus including an ion generating apparatus configured to inject ionized elements into a diagnosis subject to remove a tumor in the diagnosis subject, and an image photographing apparatus configured to measure positions of the ionized elements in the diagnosis subject, in which the ion generating apparatus includes a target including a first element and a first isotope that is a radioactive isotope of the first element, and a laser configured to allow a laser beam to be incident on the target and thus ionize the first element and the first isotope.

In an embodiment, the positions may be positions at which the ionized elements form Bragg peaks.

In an embodiment, the image photographing apparatus may measure a position of an ionized first isotope among the ionized elements.

In an embodiment, the image photographing apparatus may include positron emission tomography (PET) equipment.

In an embodiment, the target may includes about 99.9% to 99.99% of the first element and about 0.01% to 0.1% of the first isotope.

In an embodiment, number of electrons of the ionized first element may be the same as the number of the electrons of the ionized first isotope.

In an embodiment, the target may include a first portion, and a second portion, the first portion may include the first element and the first isotope, and the second portion may include a second element that is different from the first element and a second isotope that is the radioactive isotope of the second element.

In an embodiment, the target may include a first portion, and a second portion, the first portion may include the first element and the first isotope at a first ratio, and the second portion may include the first element and the first isotope at a second ratio that is different from the first ratio.

In an embodiment, the first element may include any one of carbon, fluorine, nitrogen, or oxygen.

In an embodiment of the inventive concept, a treating method using ions includes preparing a target including a first element and a first isotope that is a radioactive isotope of the first element, allowing a laser beam to be incident on the target to ionize the first element and the first isotope, allowing the ionized first element to be incident into a diagnosis subject to remove a tumor in the diagnosis subject, allowing the ionized first isotope to be incident into the diagnosis subject, and confirming positions at which the ionized elements in the diagnosis subject form Bragg peaks.

In an embodiment, the confirming of the positions of the ionized elements may include confirming a position of the ionized first isotope in the diagnosis subject, and confirming a position of the ionized first element by using the position of the ionized first isotope.

In an embodiment, the confirming of the position of the ionized first isotope may include detecting an annihilation radiation emitted from the ionized first isotope to confirm the position.

In an embodiment, the detecting of the annihilation radiation may include confirming using positron emission tomography (PET) equipment.

In an embodiment, the allowing of the ionized first element to be incident into the diagnosis subject and the allowing of the ionized first isotope to be incident into the diagnosis subject may be simultaneously performed.

In an embodiment, the allowing of the ionized first element and the ionized first isotope to be incident into the diagnosis subject, and the confirming of the position of the ionized first element may be simultaneously performed.

In an embodiment, the allowing of the ionized first element and the ionized first isotope to be incident into the diagnosis subject may be performed before the confirming of the position of the ionized first element.

In an embodiment, number of electrons of the ionized first element may be the same as the number of the electrons of the ionized first isotope.

In an embodiment, the first element may include any one of carbon, fluorine, nitrogen, or oxygen.

In an embodiment of the inventive concept, an ion generating apparatus includes a target, and a laser configured to allow a laser beam to be incident on the target and thus generate ionized elements from the target, in which the target includes a first element, and a first isotope that is a radioactive isotope of the first element.

In an embodiment, the target may include 99.9% to 99.99% of the first element and 0.01% to 0.1% of the first isotope.

In an embodiment, the first element may include any one of carbon, fluorine, nitrogen, or oxygen.

In an embodiment, the target may include a first portion, and a second portion, the first portion may include the first element and the first isotope, and the second portion may include a second element that is different from the first element and a second isotope that is the radioactive isotope of the second element.

In an embodiment, the target may include a first portion, and a second portion, the first portion may include the first element and the first isotope at a first ratio, and the second portion may include the first element and the first isotope at a second ratio that is different from the first ratio.

Details of other embodiments are included in the detailed description and the drawings.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Figure 1:
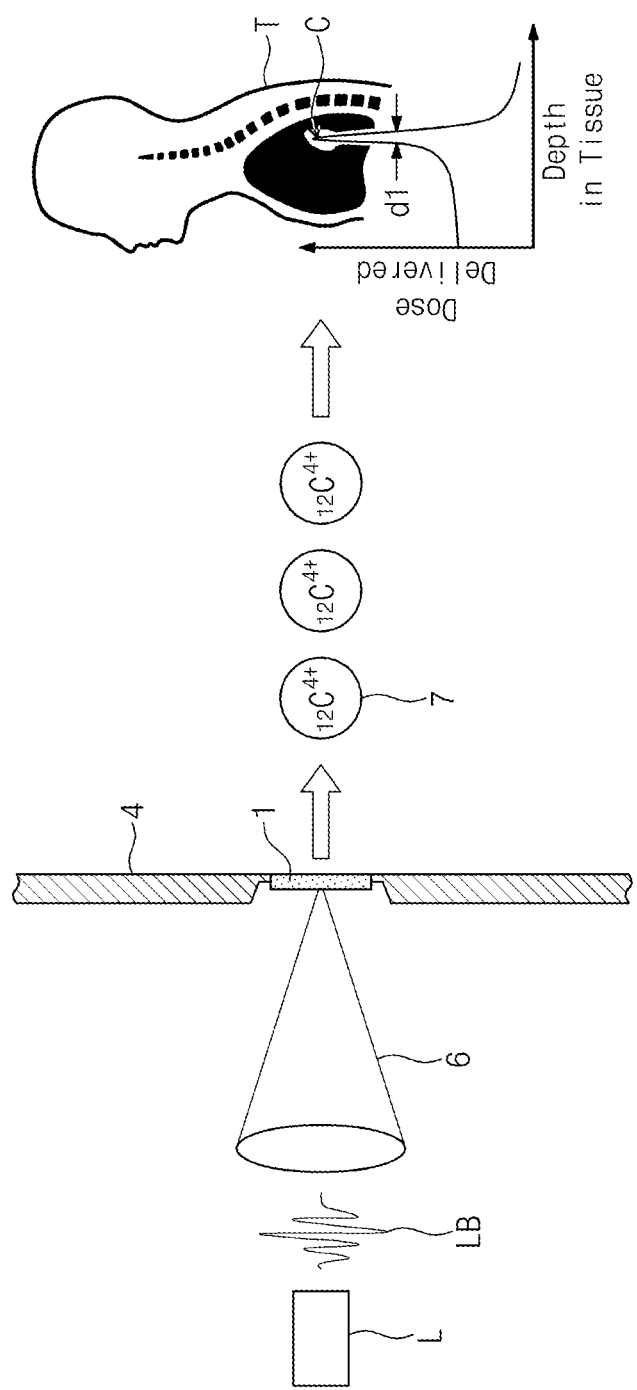
FIG. 1 is a view illustrating removal of a tumor in a diagnosis subject by using a typical ion generating apparatus.

Advantages and characteristics of the present invention, and methods for achieving them will be apparent with reference to embodiments described below in detail in addition to the accompanying drawings. However, the present invention is not limited to the embodiments to be described below but may be implemented in various forms. Therefore, the embodiments are provided to enable those skilled in the art to thoroughly understand the teaching of the present invention and to completely inform the scope of the present invention and the embodiment is just defined by the scope of the appended claims. The same elements will be designated by the same reference numerals throughout the specification.

Terms used in the specification are used to explain the embodiments and not to limit the present invention. Unless explicitly described to the contrary, a singular form includes a plural form in the present specification. "comprises" and/or "comprising" used the specification mentioned constituent members, steps, operations and/or elements do not exclude the existence or addition of one or more other components, steps, operations and/or elements.

Furthermore, embodiments described herein are described with reference to ideal cross-sectional exemplary views and/or plan views of the present invention. In the drawings, the thickness of the films and regions are exaggerated for effective description of the technical contents. Therefore, the type of the exemplary views may be modified by manufacturing techniques and/or tolerance. Thus, embodiments of the present invention also include changes in the form being generated according to the manufacturing process, not limited to the specific form shown. Accordingly, the area illustrated in the drawings have schematic properties, and shapes of the area illustrated in the drawings are not intended to limit the scope of the invention but set forth to illustrate a particular form of areas of the device.

FIG. 1 is a view illustrating removal of a tumor in a diagnosis subject T by using a typical ion generating apparatus. The ion generating apparatus allows a laser beam LB to be incident on a target 1 supported by a supporting part 4 and thus ionize elements included in the target 1. In this case, the target 1 may include a first element. As an example, the first element may be carbon C. The ionized first element 7 may be incident on a tumor portion C in the diagnosis subject T to remove the tumor. The ionized first element 7 may collide with the tumor portion C to generate active oxygen and thus disturb tumor cells of the tumor portion C, thereby hindering growth of the tumor cells or necrotizing the tumor cells. Further, disturbing of the tumor cells of the tumor portion C by the ionized first element 7 may be disturbing of the DNA double helix of the tumor cell, or disturbing of a metabolic process in a nucleus of the tumor cell. The ionized first element 7 may be set to be projected at the position of the tumor portion C, which is obtained from image diagnosis equipment, such as magnetic resonance imaging (MRI) equipment, computer tomography (CT) equipment, positron emission tomography (PET) equipment, and ultrasonic wave equipment that are equipment used to diagnose the tumor portion C of a patient. Therefore, when the ionized first element 7 reaches the tumor portion C, the ionized first element may be incident with predetermined energy to form a Bragg peak. In this case, it is required that the Bragg peak is formed at a desired position, that is, the tumor portion C, by the ionized first element 7. The ionized first element 7 may form a half-width d1 at the position at which the first element forms the Bragg peak.

Figure 2:
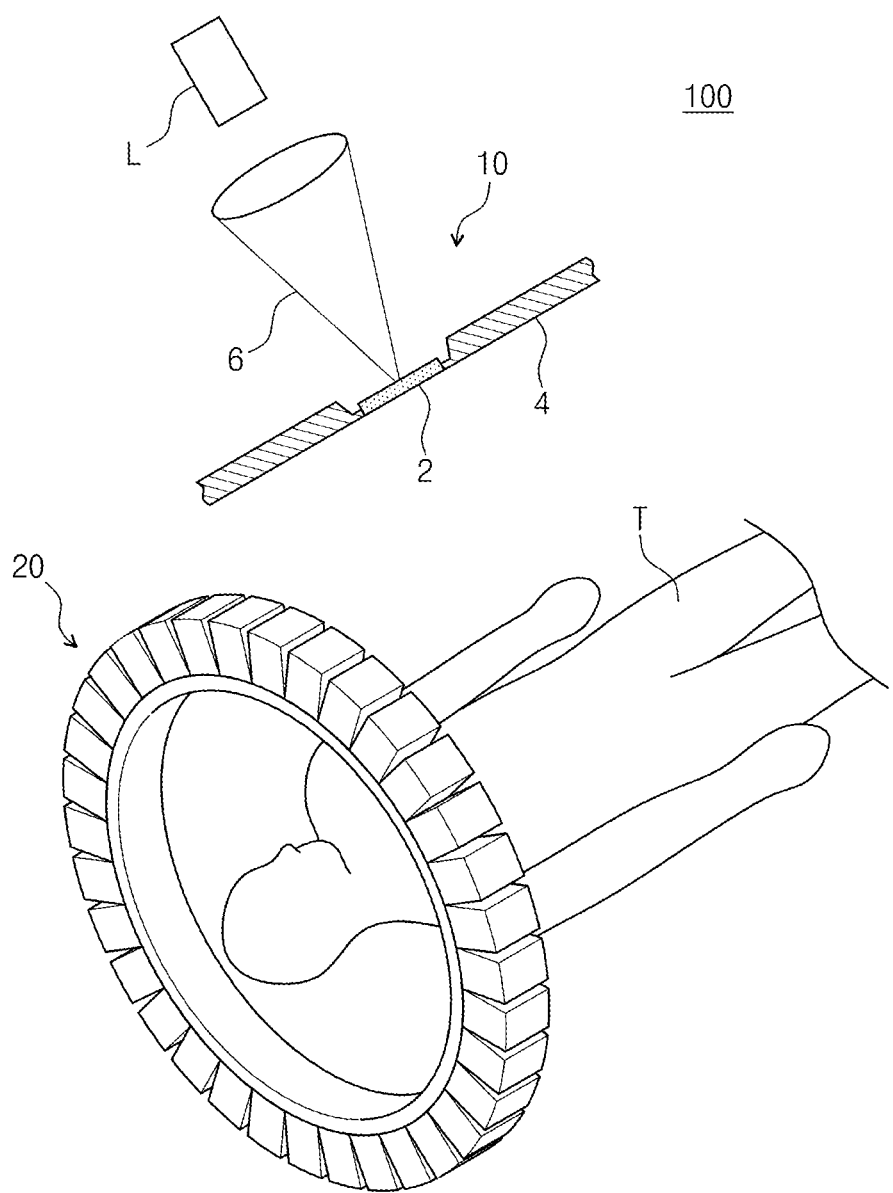
FIG. 2 is a view schematically illustrating a treating apparatus according to an embodiment of the inventive concept.
Figure 3:
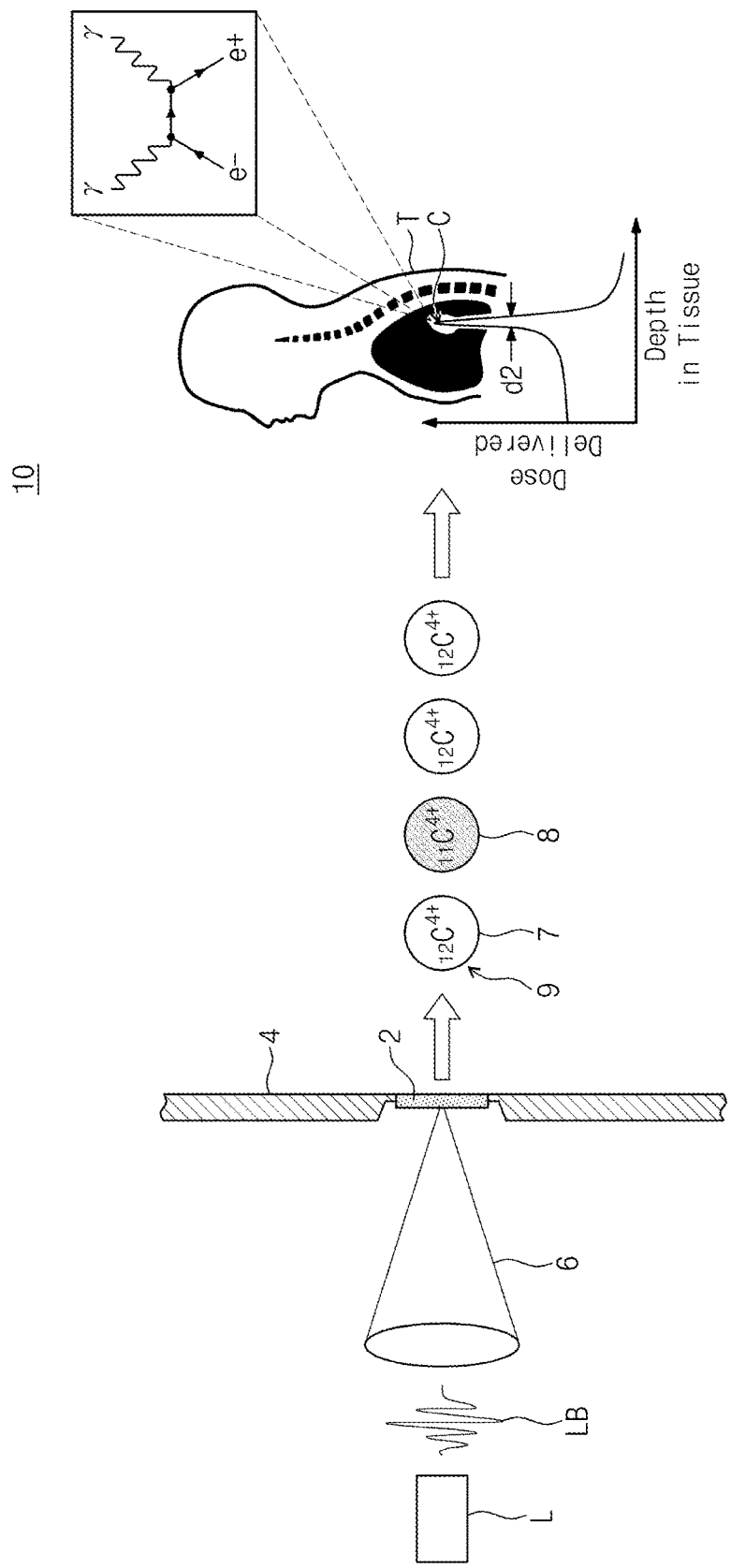
FIG. 3 is a view illustrating removal of the tumor in the diagnosis subject by using the ion generating apparatus of FIG. 2.
Figure 4:
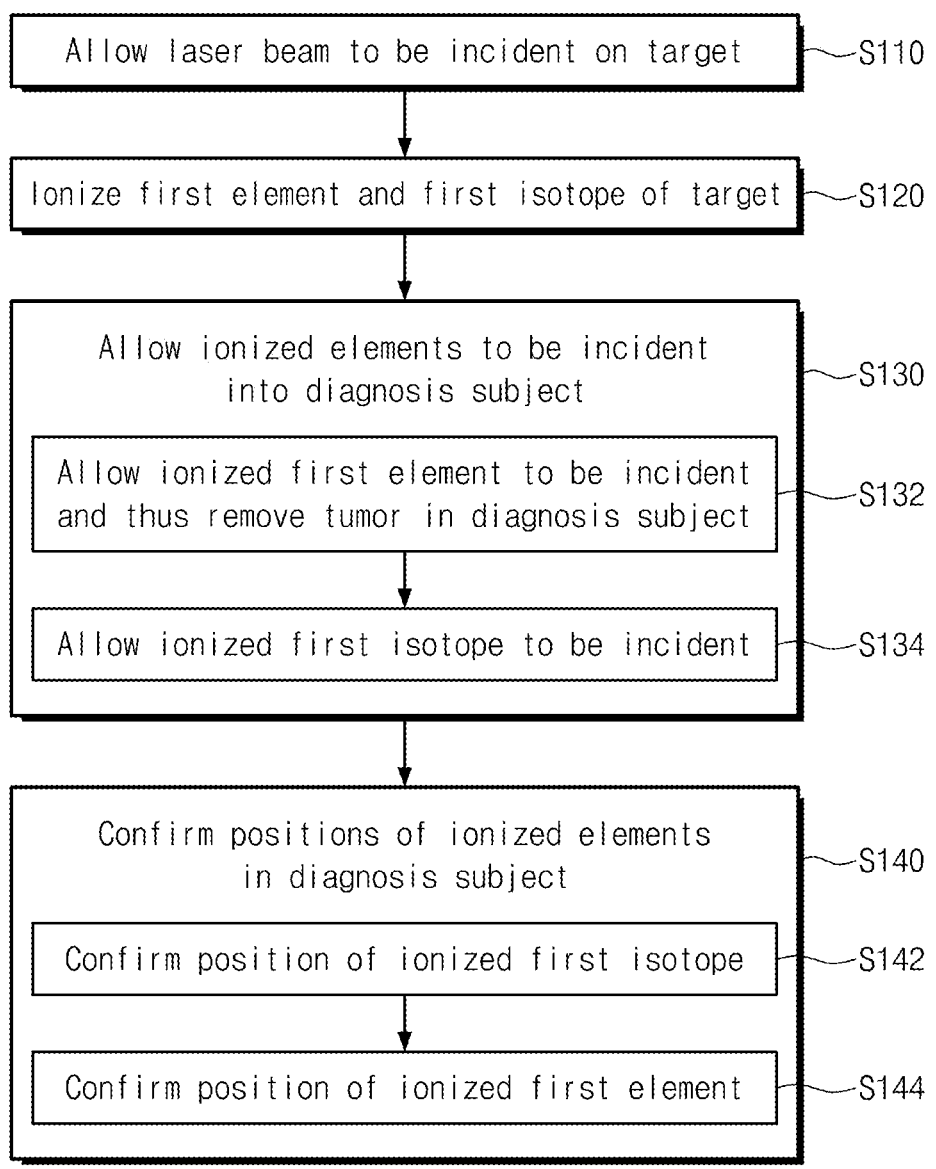
FIG. 4 is a flowchart illustrating a treating method for removing the tumor in the diagnosis subject by using the treating apparatus of FIG. 2.

FIG. 2 is a view schematically illustrating a treating apparatus 100 according to an embodiment of the inventive concept. FIG. 3 is a view illustrating removal of the tumor in the diagnosis subject T by using the ion generating apparatus 10 of FIG. 2. FIG. 4 is a flowchart illustrating a treating method for removing the tumor in the diagnosis subject T by using the treating apparatus 100 of FIG. 2. Hereinafter, the treating apparatus 100 and the treating method will be described with reference to FIGS. 2 to 4. The treating apparatus 100 may include an ion generating apparatus 10 and an image photographing apparatus 20. The treating apparatus 100 may accelerate the ions by using a laser, project the accelerated ions on the tumor portion C in the diagnosis subject T to perform treating, and image positions of the ions in the diagnosis subject T. As an example, the treating apparatus 100 may remove a cancer cell in the diagnosis subject T. The ion generating apparatus 10 and the image photographing apparatus 20 may be each independently provided, but may be provided in a combination thereof without a limitation thereto.

Referring to FIGS. 2 and 3, the ion generating apparatus 10 may include a laser L, a target 2, a supporting part 4, and an optical part 6. The laser L allows a laser beam LB to be incident on the target 2. For example, the laser beam LB may be a femtosecond laser beam. Unlike this, the laser beam LB may be a picosecond laser beam. The laser L may ionize the elements included in the target 2. The supporting part 4 may support the target 2. The target 2 may be provided in a thin film form. As an example, the target 2 may have a thickness of about 1 nm to 1 mm. The target 2 is a thin film in a thin film form, and may be provided by using a method such as chemical vapor deposition (CVD), physical vapor deposition (PVD), or electroplating. Unlike this, the target 2 may be in a gas state. The optical part 6 may focus the laser beam. As an example, the optical part 6 may be an off-axis parabola mirror. If necessary, the supporting part 4 and/or the optical part 6 may be omitted.

The target 2 may include a first element and a first isotope. The first isotope may be a radioactive isotope of the first element. As an example, the first element may be $_{12}C$ and the first isotope may be $_{11}C$. Unlike this, the first element may be $_{16}O$ and the first isotope may be $_{15}O$, or the first element may be $_{19}F$ and the first isotope may be $_{18}F$. Unlike this, the first element may be $_{14}N$ and the first isotope may be $_{13}N$. However, the first element and the first isotope are not limited thereto, and may be provided by various kinds of elements having a radioactive isotope relationship. As an example, the target 2 may includes about 99.9% to 99.99% of the first element and 0.01% to 0.1% of the first isotope.

By the laser L, ionized elements 9 are emitted from the target 2. The ionized elements 9 may include the ionized first element 7 and the ionized first isotope 8. Since the amount of the ionized first isotope 8 is insignificant as compared to the amount of the ionized first element 7, a half-width d2 formed by the ionized elements 9 may be substantially the same as a half-width d1 (of FIG. 1) formed by the ionized first element 7.

The image photographing apparatus 20 may measure the positions of the ionized elements 9 in the diagnosis subject T. As an example, the image photographing apparatus 20 may measure the position of the ionized first isotope 8 in the diagnosis subject T. The image photographing apparatus 20 may include a sensor array arranged at an angle of about 360° so as to surround the diagnosis subject T. For example, the image photographing apparatus 20 may include positron emission tomography (PET) equipment. The image photographing apparatus 20 may photograph a pair of gamma rays γ generated by an interaction of positrons emitted by the ionized first isotope 8 and electrons. In the drawings, a pair of gamma rays γ is emitted so that the gamma rays form a predetermined angle, but this is illustrated for convenience of the drawings, and actually, a pair of gamma rays γ is emitted so that the gamma rays form an angle of about 180°.

Hereinafter, the treating method for removing the tumor in the diagnosis subject T by using the treating apparatus 100 will be described. First, the target 2 including the first element and the first isotope that is the radioactive isotope of the first element is prepared (S110). As an example, the first element may be $_{12}C$ and the first isotope may be $_{11}C$. However, the first element and the first isotope are not limited thereto, and may be provided by various kinds of elements having a radioactive isotope relationship. As an example, the first element may be $_{16}O$ and the first isotope may be $_{15}O$, or the first element may be $_{19}F$ and the first isotope may be $_{18}F$. Unlike this, the first element may be $_{14}N$ and the first isotope may be $_{13}N$. The target 2 may includes about 99.9% to 99.99% of the first element and about 0.01% to 0.1% of the first isotope.

If the laser L allows the laser beam LB to be incident on the target 2, the ionized elements 9 may be generated from the target 2 (S120). The ionized elements 9 may include the ionized first element 7 and the ionized first isotope 8. In this case, the number of electrons of the ionized first element 7 and the number of electrons of the ionized first isotope 8 may be the same as each other. As an example, the ionized first element 7 may be $_{12}C^{4+}$ and the ionized first isotope 8 may be $_{11}C^{4+}$, but are not limited thereto.

The ionized elements 9 may be incident into the diagnosis subject T (S130). The ionized first element 7 may be incident into the diagnosis subject T to remove the tumor in the diagnosis subject T (S132). As an example, the ionized first element 7 may be stopped at the tumor portion C in the diagnosis subject T by a principle of the Bragg peak and may collide with the tumor portion C to generate active oxygen and thus disturb tumor cells of the tumor portion C, thereby hindering growth of the tumor cells or necrotizing the tumor cells. Further, disturbing of the tumor cells of the tumor portion C by the ionized first element 7 may be disturbing of the DNA double helix of the tumor cell, or disturbing of a metabolic process in a nucleus of the tumor cell. Accordingly, the tumor of the tumor portion C may be removed, and the diagnosis subject T may be treated. The ionized first element 7 may be set to be projected at the position of the tumor portion C, which is obtained from image diagnosis equipment, such as magnetic resonance imaging (MRI) equipment, computer tomography (CT) equipment, positron emission tomography (PET) equipment, and ultrasonic wave equipment that are equipment used to diagnose the tumor portion C of a patient. The ionized first isotope 8 may be incident into the diagnosis subject T (S134). The ionized first isotope 8 may be set to be projected at the position of the tumor portion C like the ionized first element 7. In this case, the ionized first element 7 and the ionized first isotope 8 may be simultaneously incident into the diagnosis subject T.

The positions of the ionized elements 9 in the diagnosis subject T are confirmed (S140). In this case, the positions may be positions at which the ionized elements 9 form the Bragg peaks in the diagnosis subject T. The position of the ionized first isotope 8 in the diagnosis subject T may be confirmed (S142). The position of the ionized first isotope 8 may be confirmed by using the image photographing apparatus 20. For example, the position of the ionized first isotope 8 may be confirmed by detecting an annihilation radiation emitted from the ionized first isotope. For example, the image photographing apparatus 20 may include positron emission tomography (PET) equipment. The image photographing apparatus 20 may photograph a pair of gamma rays γ generated by an interaction of positrons emitted by the ionized first isotope 8 and electrons. Thereafter, the position of the ionized first element 7 in the diagnosis subject T may be confirmed (S144). As an example, since the first element and the first isotope are different from each other in terms of only the number of neutrons, the position of the ionized first element 7 forming the Bragg peak may be substantially the same as the position of the ionized first isotope 8 forming the Bragg peak. Therefore, the position at which the gamma ray γ emitted by the ionized first isotope 8 is photographed may be judged as the position of the Bragg peak formed by the ionized first isotope 8. The allowing of the ionized elements 9 to be incident into the diagnosis subject T (S130), and the confirming of the positions of the ionized elements 9 in the diagnosis subject T (S140) may be simultaneously performed, but unlike this, the allowing of the ionized elements 9 to be incident into the diagnosis subject T (S130) may be performed before the confirming of the positions of the ionized elements 9 in the diagnosis subject T (S140). The ionized first isotope 8 may affect to remove the tumor in the diagnosis subject T like the ionized first element 7, but since the amount thereof is insignificant as compared to the ionized first element 7, the ionized first isotope 8 may serve as an indicator providing position information in the diagnosis subject T.

Figure 5:
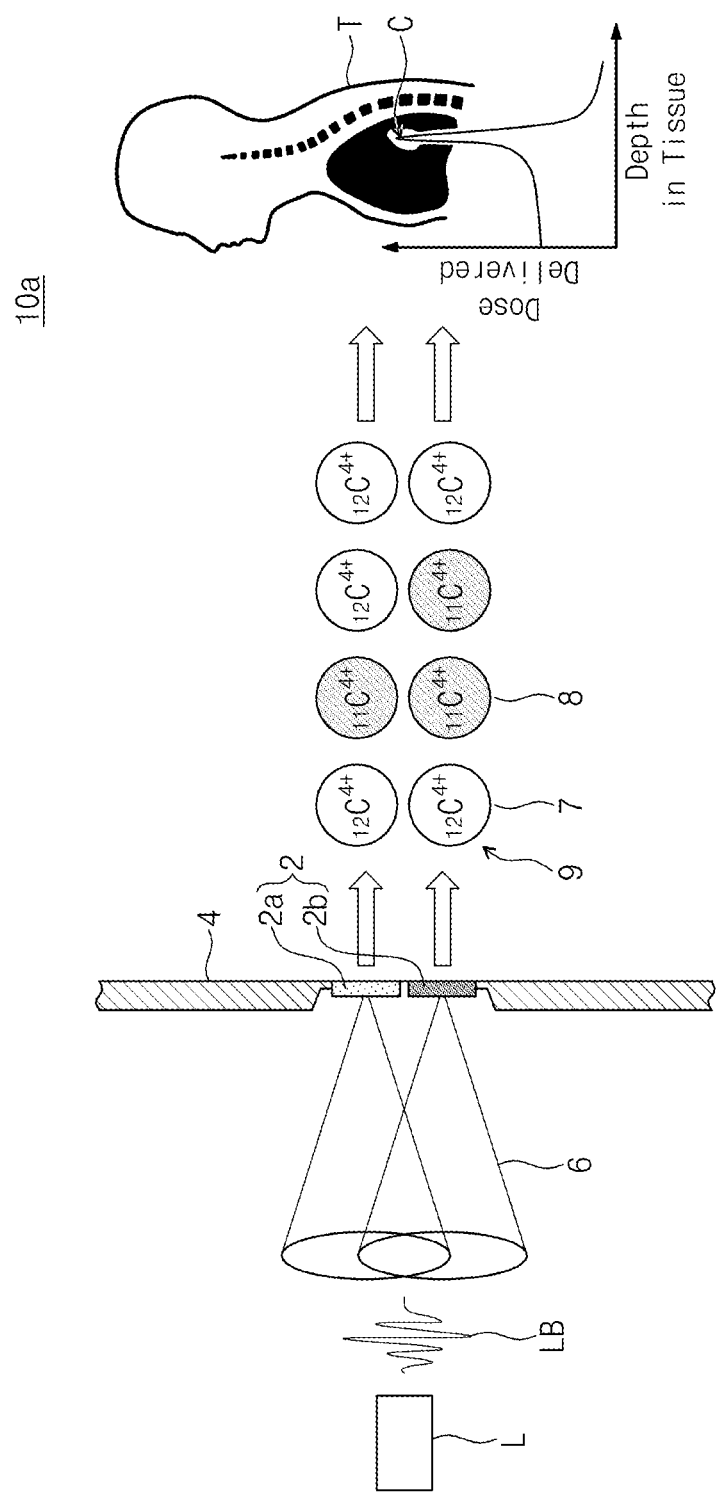
FIG. 5 is a view illustrating the ion generating apparatus according to the embodiment of the inventive concept.

FIG. 5 is a view illustrating the ion generating apparatus 10*a* according to the embodiment of the inventive concept. The same reference numerals denote constitutions that are substantially the same as the ion generating apparatus 10 described by using FIGS. 2 and 3, and an overlapping description may be omitted for simplification of the description. The target 2 of the ion generating apparatus 10*a* may include a plurality of portions. As an example, the target 2 may include a first portion 2*a* and a second portion 2*b*. The first portion 2*a* may include the first element and the first isotope at a first ratio, and the second portion 2*b* may include the first element and the first isotope at a second ratio. The second portion 2*b* may include the first isotope in a larger amount as compared to the first portion 2*a*. As an example, the first portion 2*a* may include 99.95% to 99.99% of the first element and about 0.01% to 0.05% of the first isotope, and the second portion 2*b* may include about 99.95% to 99.9% of the first element and 0.05% to 0.1% of the first isotope. However, the first ratio and the second ratio are just examples, but are not limited thereto, and may be various. Therefore, among the ionized elements 9, the amount of the ionized first isotope 8 emitted from the second portion 2*b* may be larger than the amount of the ionized first isotope 8 emitted from the first portion 2*a*. Therefore, the ion generating apparatus 10*a* may selectively adopt the portions 2*a* and 2*b* of the target 2, having different ratios. As an example, in the case where precise position information of the ionized elements 9 in the diagnosis subject T is required, the second portion 2*b* may be selected rather than the first portion 2*a* to be used, and in the case where removal of the tumor in the diagnosis subject T needs to be performed by priority, the first portion 2*a* may be selected rather than the second portion 2*b* to be used. In the embodiment of the inventive concept, the case where the target 2 has two portions is described as an example, but the target 2 may include three or more portions.

Figure 6:
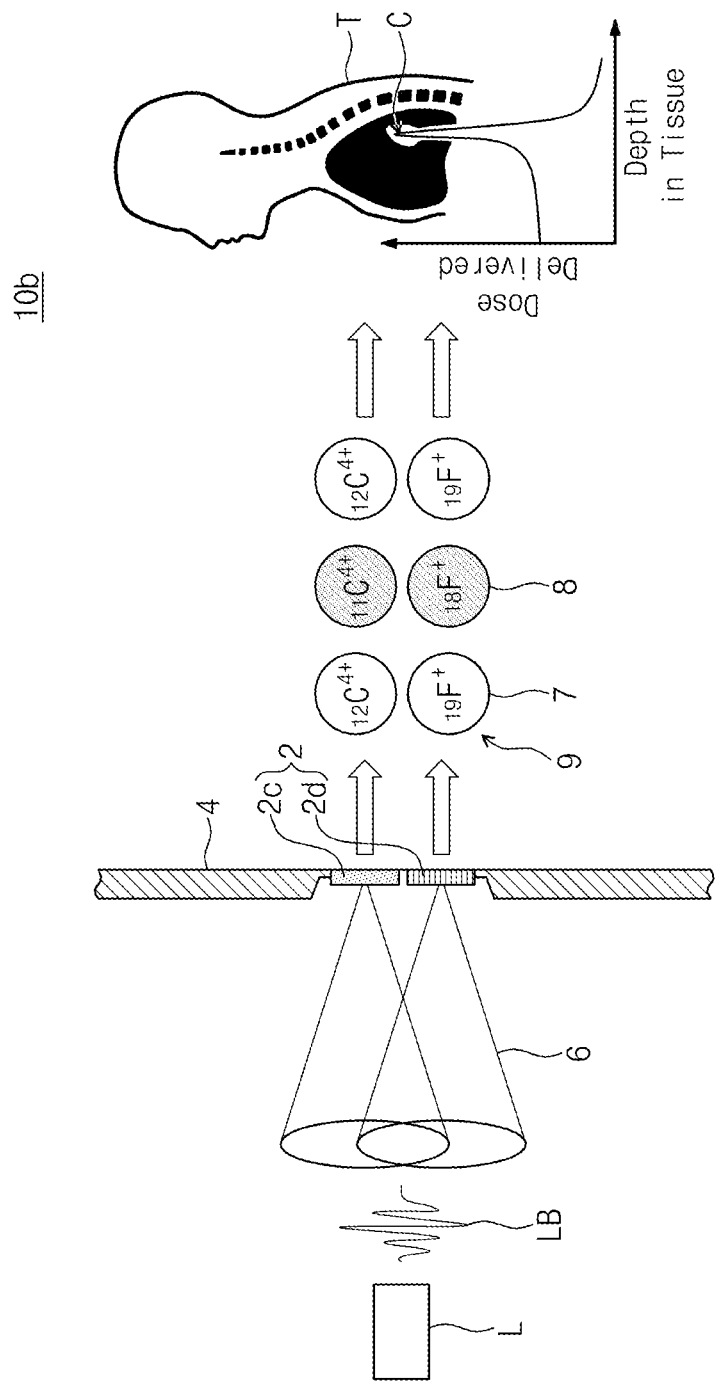
FIG. 6 is a view illustrating the ion generating apparatus according to the embodiment of the inventive concept.

FIG. 6 is a view illustrating the ion generating apparatus 10*b* according to the embodiment of the inventive concept. The same reference numerals denote constitutions that are substantially the same as the ion generating apparatus 10 described by using FIGS. 2 and 3, and an overlapping description may be omitted for simplification of the description. The target 2 of the ion generating apparatus 10*b* may include a plurality of portions. As an example, the target 2 may include a third portion 2*c* and a fourth portion 2*d*. The third portion 2*c* may include the first element and the first isotope, and the fourth portion 2*d* may include a second element and a second isotope that is a radioactive isotope of the second element. The first element and the second element may be different elements. As an example, the first element may be $_{12}C$ and the first isotope may be $_{11}C$, and the second element may be $_{19}F$ and the second isotope may be $_{18}F$. However, the first element and the second element are just examples, but are not limited thereto, and may have various combinations of elements. Therefore, the ion generating apparatus 10*b* may selectively adopt the portions 2*c* and 2*d* of the target 2, having different elements. As an example, according to a kind or a half-life of elements used to remove the tumor in the diagnosis subject T, the portions 2*c* and 2*d* of the target 2, having the different elements, may be selectively used. In the embodiment of the inventive concept, the case where the target 2 has two portions is described as an example, but the target 2 may include three or more portions.

According to the embodiment of the inventive concept, by together injecting the first element for removing the tumor and the first isotope that is the radioactive isotope of the first element into the diagnosis subject T, tumor removal position information may be obtained while the tumor is removed. Therefore, a tumor removal process may be understood in real time, and a resulting feedback may be feasible.

According to the embodiment of the inventive concept, by together injecting the first element and the first isotope that is the radioactive isotope of the first element into the diagnosis subject, tumor removal position information may be obtained while the tumor is removed. Therefore, a tumor removal process may be understood in real time, and a resulting feedback may be feasible.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:

1. A treating apparatus comprising:
an ion generating apparatus configured to inject ionized elements into a diagnosis subject to remove a tumor in the diagnosis subject; and
an image photographing apparatus configured to measure positions of the ionized elements in the diagnosis subject,
wherein the ion generating apparatus includes:
a target including a first element and a first isotope that is a radioactive isotope of the first element; and
a laser configured to allow a laser beam to be incident on the target and thus ionize the first element and the first isotope.

2. The treating apparatus of claim 1, wherein the positions are positions at which the ionized elements form Bragg peaks.

3. The treating apparatus of claim 2, wherein the image photographing apparatus measures a position of an ionized first isotope among the ionized elements.

4. The treating apparatus of claim 3, wherein the image photographing apparatus includes positron emission tomography (PET) equipment.

5. The treating apparatus of claim 1, wherein the target includes about 99.9% to 99.99% of the first element and 0.01% to 0.1% of the first isotope.

6. The treating apparatus of claim 1, wherein number of electrons of the ionized first element is the same as the number of the electrons of the ionized first isotope.

7. The treating apparatus of claim 1, wherein the target includes
a first portion; and
a second portion,
wherein the first portion includes the first element and the first isotope, and the second portion includes a second element that is different from the first element and a second isotope that is the radioactive isotope of the second element.

8. The treating apparatus of claim 1, wherein the target includes
a first portion; and
a second portion,
wherein the first portion includes the first element and the first isotope at a first ratio, and the second portion includes the first element and the first isotope at a second ratio that is different from the first ratio.

9. The treating apparatus of claim 1, wherein the first element includes any one of carbon, fluorine, nitrogen, or oxygen.

10. A treating method comprising:
preparing a target including a first element and a first isotope that is a radioactive isotope of the first element;
allowing a laser beam to be incident on the target to ionize the first element and the first isotope;
allowing the ionized first element to be incident into a diagnosis subject to remove a tumor in the diagnosis subject;
allowing the ionized first isotope to be incident into the diagnosis subject; and
confirming positions at which the ionized elements in the diagnosis subject form Bragg peaks.

11. The treating method of claim 10, wherein the confirming of the positions of the ionized elements includes:
confirming a position of the ionized first isotope in the diagnosis subject; and
confirming a position of the ionized first element by using the position of the ionized first isotope.

12. The treating method of claim 11, wherein the confirming of the position of the ionized first isotope includes detecting an annihilation radiation emitted from the ionized first isotope to confirm the position.

13. The treating method of claim 12, wherein the detecting of the annihilation radiation includes confirming using positron emission tomography (PET) equipment.

14. The treating method of claim 10, wherein the allowing of the ionized first element to be incident into the diagnosis subject and the allowing of the ionized first isotope to be incident into the diagnosis subject are simultaneously performed.

15. The treating method of claim 10, wherein the allowing of the ionized first element and the ionized first isotope to be incident into the diagnosis subject, and the confirming of the position of the ionized first element are simultaneously performed.

16. The treating method of claim 10, wherein the allowing of the ionized first element and the ionized first isotope to be incident into the diagnosis subject is performed before the confirming of the position of the ionized first element.

17. The treating method of claim 10, wherein number of electrons of the ionized first element is the same as the number of the electrons of the ionized first isotope.

18. The treating method of claim 10, wherein the first element includes any one of carbon, fluorine, nitrogen, or oxygen.

19. An ion generating apparatus comprising:
a target; and
a laser configured to allow a laser beam to be incident on the target and thus generate ionized elements from the target,
wherein the target includes:
a first element; and
a first isotope that is a radioactive isotope of the first element.

20. The ion generating apparatus of claim 19, wherein the target includes 99.9% to 99.99% of the first element and about 0.01% to 0.1% of the first isotope.

21. The ion generating apparatus of claim 19, wherein the first element includes any one of carbon, fluorine, nitrogen, or oxygen.

22. The ion generating apparatus of claim 19, wherein the target includes
a first portion; and
a second portion,
wherein the first portion includes the first element and the first isotope, and the second portion includes a second element that is different from the first element and a second isotope that is the radioactive isotope of the second element.

23. The ion generating apparatus of claim 19, wherein the target includes
a first portion; and
a second portion,
wherein the first portion includes the first element and the first isotope at a first ratio, and the second portion includes the first element and the first isotope at a second ratio that is different from the first ratio.

* * * * *